United States Patent
Künnecke et al.

(10) Patent No.: US 7,790,438 B2
(45) Date of Patent: Sep. 7, 2010

(54) APPARATUSES AND METHODS FOR DETECTING AN ANALYTE

(75) Inventors: Wolfgang Künnecke, Braunschweig (DE); Michael Hartlep, Braunschweig (DE); Jens Giesenberg, Wolfenbüttel (DE)

(73) Assignee: TRACE Analytics GmbH, Braunschweig (DE)

(*) Notice: Subject to any disclaimer, the term of this patent is extended or adjusted under 35 U.S.C. 154(b) by 372 days.

(21) Appl. No.: 11/766,246

(22) Filed: Jun. 21, 2007

(65) Prior Publication Data

US 2008/0241966 A1 Oct. 2, 2008

(30) Foreign Application Priority Data

Jun. 21, 2006 (EP) ................... 06115843

(51) Int. Cl.
*C12M 3/00* (2006.01)
(52) U.S. Cl. .......... 435/286.5; 436/52; 422/68.1; 422/103; 422/110; 422/115
(58) Field of Classification Search .......... None
See application file for complete search history.

(56) References Cited

U.S. PATENT DOCUMENTS

| | | | |
|---|---|---|---|
| 3,661,010 A | 5/1972 | Neuwelt | |
| 3,983,864 A | 10/1976 | Sielaff et al. | |
| 4,221,567 A | 9/1980 | Clark et al. | |
| 5,058,416 A | 10/1991 | Engelhardt et al. | |
| 2002/0045272 A1* | 4/2002 | McDevitt et al. | 436/518 |
| 2005/0221373 A1* | 10/2005 | Enzelberger et al. | 435/6 |
| 2006/0009727 A1 | 1/2006 | O'Mahony et al. | |

FOREIGN PATENT DOCUMENTS

| | | |
|---|---|---|
| EP | 0098550 | 1/1984 |
| EP | 0251027 | 7/1988 |
| EP | 0367752 | 10/1989 |
| EP | 0475534 | 3/1992 |
| EP | 0940151 | 8/1999 |
| WO | 2005042059 | 5/2005 |

* cited by examiner

*Primary Examiner*—N Yang
(74) *Attorney, Agent, or Firm*—Roylance, Abrams, Berdo & Goodman, L.L.P.

(57) ABSTRACT

A method and apparatus for detecting an analyte includes a sensor chamber for detecting an analyte, an analyte feed chamber, a distributor, and a controller for controlling the transport medium flow. The distributor includes an annular channel with four connections with a switchable isolating device between two connections. The controller controls the distributor for flushing the transport medium fed from the distributor to the sensor chamber without passing through the analyte feed chamber and for measuring the transport medium fed from the distributor to the sensor chamber while passing through the analyte feed chamber.

10 Claims, 6 Drawing Sheets

APPARATUSES AND METHODS FOR DETECTING AN ANALYTE

FIELD OF THE INVENTION

The present invention relates to apparatuses and methods for detecting an analyte.

BACKGROUND OF THE INVENTION

In process technology and medicine it is often necessary to determine the presence and possibly also the concentration of a preselected analyte rapidly and as continuously as possible. A number of probes and sensors are used for this purpose. For example, an immersion probe is known from WO 00/25107, which is immersed in an analyte containing medium—for example the interior of a bioreactor—and an analyte is detected therein. The immersion probe is separated from the medium to be analysed by a membrane that is permeable to the analyte. It has however been found disadvantageous, in particular when monitoring a bioreactor, that with this design of analysis apparatus it is no longer possible to dilute the analyte to be analysed. Accordingly, only those sensors whose maximum measurement range is greater than the highest analyte concentration to be expected can realistically be used. The sensor would otherwise always display the maximum measurement value irrespective of the actual analyte concentration. With this analysis apparatus the measurement range within which the concentration of the analyte can be determined is therefore restricted.

This is particularly disadvantageous when monitoring biotechnological and medical processes, for example in a continuous monitoring of the blood sugar level of a diabetic patient. Especially with diabetic patients, the blood sugar concentration can fluctuate wildly within a short period of time, which requires a rapid administration of insulin that is accurately matched to the respective blood sugar concentration. There is therefore a constant need, specifically in medicine and biotechnology, for rapid, sensitive and accurate analysis methods for monitoring of the preselected analytes, as well as corresponding apparatuses.

In this connection EP 0 441 179 A1 discloses a portable analysis apparatus for the continuous determination of the glucose concentration in the blood of a diabetic patient over a period of 24 to 36 hours. The analysis apparatus includes a microdialysis needle that is introduced via a venous catheter into a vein of the patient to be monitored. The microdialysis needle includes a glucose-permeable dialysis membrane, so that glucose from the patient's blood can diffuse into a space located behind the dialysis membrane. This space is constantly flushed out by a dialysis fluid, the glucose-containing dialysis fluid being passed to a sensor. The sensor is installed in a portable apparatus, which also contains a reservoir of dialysis fluid and a receptacle for spent dialysis fluid. The sensor is connected to the microdialysis needle via a very thin flexible tube with an internal diameter of 0.1 mm, in order to allow a rapid transport of glucose from the micodialysis needle to the sensor. A disadvantage of this apparatus however is that the very thin flexible tube generates a very high transport resistance and therefore pressure, which means that there is a danger that the dialysis membrane or the flexible tube will rupture. A further disadvantage is the fact that there is no possibility of carrying out a null line (base line) adjustment of the sensor during the operation of the analysis apparatus. There is therefore the danger that the measurement accuracy of the sensor will be impaired over long periods of use.

From U.S. Pat. No. 6,852,500 B1 an analysis method is known for deterring the glucose concentration in a body fluid. In this case a dialysis fluid is pumped in a pulsed manner to a sensor through a dialysis cell which on one side is in contact with the glucose-containing body fluid to a sensor, which in one pulse is glucose-free and accordingly can receive glucose from the body fluid via the dialysis membrane, and which is a further pulse contains a known glucose concentration. In this way it should be possible to measure the glucose concentration in the body fluid to be analysed at intervals of in each case 9 minutes. A disadvantage of this method is on the one hand the relatively slow cycle time of 9 minutes, and on the other hand also the complicated control of the method and the high consumption of dialysis fluid due to repeated administration of a dialysis solution of known glucose concentration.

DE 27 37 922 A1 again discloses an analysis apparatus for monitoring a blood glucose concentration. The analysis apparatus again has a dialysis membrane for separating glucose from further blood constituents. The dialysis fluid should in this connection be cycled via an enzymatic glucose sensor (glucose oxidase with oxygen electrode) through the dialysis membrane. If necessary a calibration solution can be metered in, in a pulsed manner. The disadvantage however is that due to the closed cycle of the dialysis fluid during the conventional operation of such an apparatus. A complete equilibration of the concentration of glucose in the dialysis fluid and in the blood of a monitored patient occurs, so that the sensor is again to some extent loaded with very high glucose concentrations. Accordingly the sensor must have a very wide measurement range, or must be correspondingly insensitive. Due to the high operation stress on the sensor there is also the danger that the latter will quickly become inactivated.

U.S. Pat. No. 4,245,634 discloses an analysis apparatus in the form of an artificial pancreas, in which blood diluted by infusion with heparin solution is taken from a patient through a double-bore catheter and the blood glucose concentration is measured photometrically. The disadvantage in this case is that the measurement accuracy depends on the pumping rate of the infused heparin solution. In addition there are no possibilities of performing calibrations.

US 2006/0009727 A1 discloses an analysis apparatus for the extra-corporeal determination of a blood glucose concentration. In this case circulating blood is taken from a patient through a double-bore catheter and a glucose-containing ultrafiltrate is separated via an ultrafiltration unit, the ultrafiltrate being passed to a glucose sensor. The ultrafiltrate is collected and reinfused into the patient from time to time in order to keep the volume loss of blood fluid low. For purposes of calibration a calibration fluid is fed in through a calibration sensor. Whereas in normal operation the calibration sensor is flushed with ultrafiltrate, for the calibration the flow direction is reversed, the ultrafiltrate is forced back into the ultrafiltration unit and the calibration sensor is charged with calibration fluid. The disadvantage of this arrangement is the complicated construction of the apparatus and the need to force the ultrafiltrate back into the ultrafiltration unit for purposes of calibration.

SUMMARY OF THE INVENTION

An object of the present invention was accordingly to provide an apparatus and a method for detecting an analyte. The apparatus should be of as simple a design as possible, should be easy to maintain, should permit a rapid measurement of an analyte concentration, and should as far as possible be suitable for use in treating a human or animal and/or should have an adjustable sensitivity.

According to the invention an analysis apparatus is therefore provided, comprising
- a) a sensor chamber with a sensor for detecting an analyte in a transport medium,
- b) an analyte feed chamber for receiving the analyte in the transport medium,
- c) a distributor in flow communication with the sensor chamber and the analyte feed chamber, and
- d) a control means for controlling a transport medium flow, wherein the distributor comprises:

(c1) an annular channel with four connections arranged spaced apart from one another, and wherein (c2) the distributor includes in each case a switchable isolating means between two adjacent connections, and the control means is configured to control the distributor in such a way that
- for the flushing, the transport medium is fed from the distributor to the sensor chamber without passing through the analyte feed chamber, and
- for the measurement, the transport medium is fed from the distributor to the sensor chamber while passing through the analyte feed chamber.

DETAILED DESCRIPTION OF THE INVENTION

The apparatus according to the invention enables in a simple way the fluid volume between the analyte feed chamber and sensor chamber to be kept low and accordingly enables a rapid determination of the analyte concentration to be carried out. In addition the sensor chamber and the analyte feed chamber can be completely rinsed out with a very small volume of a rinse liquid, which also contributes to a rapid measurement of an analyte concentration. In addition the apparatus also enables the sensor to be re-calibrated by using a suitably calibrated solution when rinsing the sensor chamber, and thereby enables the measurement accuracy of the apparatus according to the invention to be maintained at a permanently high level. The apparatus according to the invention is in addition of very simple design and construction and is accordingly easy to operate and maintain.

By using switchable isolating means it is possible to reverse the flow direction of the transport medium in the sensor chamber without having to reverse the pumping direction of a pump that is always present in order to move the transport medium. Accordingly, the transport medium can always be moved just by suction or just by excess pressure in the distributor and correspondingly also in the sensor chamber. This avoids the sharp pressure variations of the transport medium occurring when the pumping direction is reversed and also avoids the resultant excessive loading of the sensor or sensors of the sensor chamber and/or of a membrane of the analyte feed chamber. Apparatuses in which a reversal of the pumping direction or other sharp pressure variations of the transport medium necessarily occur are disclosed for example in the specifications U.S. Pat. No. 4,221,567, EP 0 940 151 A1, EP 0 367 752 A1 and U.S. Pat. No. 3,983,864. It is also advantageous that a high-maintenance rotary valve such as is used for example in EP 0 098 550 A2, WO 2005/042059 A2 and EP 0 251 027 A can be dispensed with when using a distributor as provided for according to the invention.

In particular the distributor and optionally also the analyte feed chamber and/or the sensor chamber may be designed as disposable articles. In addition the distributor, the analyte feed chamber and the sensor chamber are preferably designed as an independent structural part that can be connected to the other elements of the apparatus according to the invention. When the distributor, the analyte feed chamber and the sensor chamber is worn out, the respective structural part can simply be replaced and operation of the apparatus according to the invention can quickly be resumed.

In preferred embodiments of the analysis apparatus according to the invention each of the controllable isolating means between two adjacent connections is or includes a valve that can be controlled by the pressure of a control fluid or magnetically.

Such an equipped distributor may be composed of advantageously few individual structural parts. Such a distributor has small dimensions and can be connected up quickly, and it is easy to clean and maintain. Furthermore, it can easily be sterilised and is particularly suitable for keeping the transport medium sterile.

Particularly preferred is a distributor with an isolating means which includes a membrane for closing the annular channel at the respective isolating means. Preferably each of the isolating means has a corresponding membrane. It is particularly preferred if the membrane is common to all isolating means and is made in one part. A membrane can be subjected particularly easily via a control channel to the pressure of a control fluid—preferably compressed air—and thus be switched very easily, quickly and in a low-maintenance manner. The isolating means of the distributor according to the invention in particularly preferred embodiments do not involve any movable parts up to the movable membrane, and are then particularly low-maintenance.

The distributor accordingly comprises four switching points for allowing or connecting the flow of the transport medium through the respective switching point of the annular channel. Conveniently the distributor can be switched to at least two distributor states. In a first, rinse switching state, a pair of switching points are closed, an open switching point then being arranged in each case between two closed switching points. The distributor is designed so that, together with the sensor chamber and the analyte feed chamber, fluid can flow in a rinsing direction in a first section of the annular channel from an inflow through an open switching point into the sensor chamber and the analyte feed chamber, and from there in a second section of the annular channel through a further open switching point into an outflow. In a second, analysis switching state, the switching points that were open in the rinse switching state are in each case now closed, and the switching points that were closed in the rinse switching state are now open. Accordingly, in the analysis switching state fluid can flow through the distributor, analyte feed chamber and sensor chamber from the inflow through an open switching point into the analyte feed chamber, from there into the sensor chamber, and from there through a further section of the annular channel and through the further open switching point into the outflow.

In a particularly preferred embodiment the distributor includes a channel base body with the annular channel arranged thereon. The annular channel is open on the side facing away from the channel base body at least at those points at which a switching is to take place, and is preferably open over its whole length on the side facing away from the channel base body. The annular channel is covered with a membrane (again at least at the points to be switched or over the whole length of the annular channel). On the side facing away from the channel base body the membrane is connected in a pressure-tight manner to a switching base body. The switching base body comprises two channels with in each case two switching openings, which connect the respective channel at a switching point of the channel base body to the membrane. By charging a switching channel with a medium that is under pressure, for example compressed air, the membrane at the switching points can be pressed into the channel of the channel base body and the channel can thereby be closed at the switching points. In this way fluid can in a simple, preselectable manner be caused to flow in one of two directions through the channel of the channel base body.

In a further preferred embodiment the distributor includes a prism-shaped and preferably cuboid-shaped channel base body, on which two halves of the annular channel are arranged on adjacent or preferably oppositely facing sides of the channel base body. The two halves of the annular channel are then connected to one another by bores or channel sections. Both sides of the channel base body, each of which comprises one half of the annular channel, are in each case provided with a switching base body, which as described above can interact via a membrane at the switching points with the channel base body in order to close the switching points.

In a further preferred embodiment the distributor includes a channel base body on or in which the annular channel is arranged. The isolating means are formed by switchable magnetic valves. In addition the distributor includes a switching base body with control connections for the magnetic valves for purposes of control.

Regardless of the respective embodiment of the distributor, the annular channel has a channel base body and preferably in addition all channels that connect the annular channel to the analyte feed chamber and sensor chamber, and the sensor chamber to the analyte feed chamber, preferably have an internal diameter of 0.01 to 1 mm and particularly preferably an internal diameter of 0.7 to 0.9 mm, and thus allow a throughflow of an aqueous transport medium, preferably as described hereinbelow, of 1-1.5 m/l per minute. When using channels of rectangular or other cross-section, the cross-sectional area is preferably dimensioned as in the case of a channel with an internal diameter of 0.01 to 1 mm and preferably of 0.7 to 0.9 mm. Conveniently the walls of the channels and of the sensor and analyte feed chambers in contact with the transport medium are inert with respect to the analyte and in addition prevent any significant adsorption of the analyte on the walls.

If a channel cross-section of 0.01 to 1 mm and in particular of 0.7 to 0.9 mm is employed, very sharply resolved peak-shaped analyte concentration pulses can be conveyed from the analyte feed chamber to the sensor chamber and measured there. The concentration pulses then act so as to generate a peak-shaped signal by the sensor of the sensor chamber. The sensor signal can be evaluated via the height, surface area or gradient of the signal or signal slopes. Furthermore, with the aforementioned internal diameters and the corresponding channel cross-sectional areas, only small amounts of the transport medium are needed to transport the analyte from the analyte feed chamber to the sensor chamber. If in addition the sensor chamber and the analyte feed chamber are arranged close to one another so that the length of the connecting channel is small, then a particularly rapid response behaviour of the sensor is achieved, with the result that a high measurement frequency can be obtained. With an internal channel diameter of 100 μm flow rates of for example 10 to 100 μl/min can be adjusted, in order thereby to achieve a particularly rapid transporting of the analyte from the analyte feed chamber to the sensor chamber with at the same time a low consumption of transport medium. A preferred implantable analyte feed chamber is in turn connected to the sensor chamber by a channel with an internal diameter of 10 μm, whereby in this case flow rates of a few nanoliters per minute are sufficient to transport an analyte to the sensor chamber.

Preferably the distributor is designed as a disposable structural part and can be connected to the other components of the apparatus according to the invention by releasable connections such as described above. The corresponding disposable structural part preferably includes the whole annular channel of the distributor according to the invention, particularly preferably in the form of a channel base body as described above. In further preferred embodiments the disposable structural part also includes the one or more membranes for closing the switching points of the distributor and one or more switching base bodies, in particular as described above. The membrane or membranes and the switching base body or bodies can in this connection be rigidly connected to the channel base body or can be designed as structural parts that can be connected to the latter.

Preferably a distributor designed as a disposable structural part includes in addition a sensor chamber and/or an analyte feed chamber.

In preferred embodiments of the invention the sensor chamber includes one, two, three or more sensors.

Each sensor of the sensor chamber of an apparatus according to the invention is preferably selected from the group consisting of electrochemical sensors and optical sensors, in particular amperometric sensors, conductivity sensors, potentiometric sensors, biosensors, oxygen sensors and enzyme sensors. The apparatus according to the invention has a very broad field of application if an appropriate sensor is used and is also extremely versatile. By a suitable choice of sensor the apparatus can be adapted to the respective analyte and to the analyte concentration to be expected.

It is also preferred if the analyte feed chamber includes one or more sensors as described above. In this way analyses can be carried out directly in the analyte feed chamber. The sensor or sensors can be arranged on the side of the medium to be analysed and/or on the transport medium side. If a sensor is arranged on the side of the medium to be analysed, it can preferably be sterilised or separated by a sterile filter from the medium to be analysed. In this way contamination of the medium to be analysed due to the sensor or sensors can be prevented.

The analyte feed chamber defines a volume of the transport medium and allows the analyte to pass from a medium to be analysed that is outside the analyte feed chamber into the transport medium inside the analyte feed chamber. In a preferred apparatus according to the invention the analyte feed chamber is connected to a medium to be analysed via a membrane which allows the passage of the analyte from the medium to be analysed into the transport medium, but prevents other substances from passing to the transport medium. The analyte feed chamber may in particular have the configuration of a dialysis chamber. The membrane is preferably a dialysis membrane or filter membrane for separating the analyte from the medium to be analysed. The analyte feed chamber may for example and preferably be designed as an immersion probe with a membrane that can be immersed in the medium to be analysed. The apparatus according to the invention thus enables a sample of the analyte to be taken, practically without any loss of fluid, from the medium to be analysed. According to the invention a membrane is preferably used which allows the passage of molecules up to a size of 50000 Da and particularly preferably up to a size of 12000 Da. The analyte feed chamber may also contain a gas diffusion membrane for separating the analyte from a gaseous medium to be analysed. The gas diffusion membrane is preferably a porous polypropylene membrane or Teflon membrane.

By using an appropriate membrane in the analyte feed chamber, particularly preferred analytes such as glucose, fructose, sucrose, glycerol, methanol, glutamine, glutamate, phosphate, lactate, lactose, ammonium, ethanol, an antibody, pesticide, antibiotic, protein content, fat content, water content, $pO_2$, $pCO_2$ and/or pH can be determined particularly well. Particularly preferred media to be analysed are liquid microbiological media, in particular a nutrient medium of a bioreactor, and physiological media, in particular body fluids such as blood and lymph. Further preferred media to be analysed include a gaseous media such as respiratory air or feed air or waste air of a bioreactor.

The analyte feed chamber has in preferred embodiments a channel with a width of 1.1-1.5 mm, measured at the contact point with the (dialysis or gas diffusion) membrane, and a depth of 0.3 to 1 mm, and the channel volume underneath the membrane is preferably 7 to 35 µl. If the analyte has a tendency to form blockages or plaques in the channel of the analyte feed chamber or at other sites of the apparatus according to the invention, suitably larger channel diameters and volumes of the analyte feed chamber and/or sensor chamber are chosen.

Also preferred is an analyte feed chamber in the form of a hollow fibre or a bundle of hollow fibres that can be flushed out by the transport medium. The hollow fibre(s) is/are immersed in a surrounding, preferably liquid or gaseous medium to be analysed, the analyte being able to pass through the fibre wall into the transport medium. As regards the design and construction of suitable analyte feed chambers, the person skilled in the art will preferably turn to the hollow fibre bundles that are conventionally used in haemodialysis or in blood oxygenators.

During the sampling from the medium to be analysed the analyte feed chamber can be rinsed out with the transport medium. This is particularly advantageous in the case where the analyte concentration in the transport medium is to be kept low. The analyte feed chamber may however also be filled with a standing transport medium, so that the analyte in the analyte feed chamber is enriched. On the basis of the flow velocity and the residence time of the transport medium in the analyte feed chamber, the concentration of the analyte in the medium to be analysed can then be calculated. The apparatus according to the invention accordingly enables in a particularly simple way the analyte to be diluted or concentrated to a preselected concentration range before it is conveyed to the sensor chamber, by subjecting the analyte feed chamber in each case to a preselected flow velocity or a preselected residence time of the transport medium. The apparatus according to the invention is accordingly suitable for carrying out reliable analyte concentration determinations also in the case of rapidly varying analyte concentrations of the medium to be analysed, without having to dilute the medium itself to be analysed or having to use an altered sensor. The apparatus according to the invention accordingly allows particularly precise measurements to be made in a wide concentration range of an analyte.

In preferred embodiments the sensor chamber and the distributor are contained in a unitary structural body. The apparatus according to the invention can be miniaturised particularly easily and accordingly can be used for numerous intended applications. The apparatus according to the invention can in particular be used to monitor a concentration behaviour, for example in a bioreactor or in a patient, in particular a person or animal, for example to measure the blood glucose concentration. The apparatus according to the invention can advantageously be easily sterilised and maintained sterile by the use of an analyte feed chamber with a membrane that permits the passage of the analyte from the medium to be analysed into the transport medium.

The apparatus according to the invention and in particular the unitary structural body can be miniaturised extremely effectively. Preferably the apparatus according to the invention therefore has a unitary structural body with external dimensions of the structural body of up to 4×8×3 cm, preferably 2×3×0.5 cm, the structural body being counted as that structural part which contains the sensor chamber and the distributor in addition to control channels for the switching points of the distributor, but excluding connections and feed lines and discharge lines to and from the distributor.

According to the invention an analysis method is also provided, in particular for operating an apparatus according to the invention, said method comprising the pumping of a transport medium in a pumping direction, and including the following steps:

rinsing a sensor for the substance to be analysed with the transport medium in a first flow direction, the transport medium being passed to an analyte feed chamber after the rinsing of the sensor, charging the transport medium in the analyte feed chamber with an amount of the analyte to be detected, and without switching the pumping direction, reversing the flow direction of the transport medium in order to convey the transport medium, possibly charged with analyte, from the analyte feed chamber to the sensor.

By the use of the method according to the invention the advantages described above of the apparatus according to the invention can be achieved. In particular only a small amount of fluid is required for charging the sensor with the analyte-containing transport medium and also for rinsing the sensor. The method according to the invention thus permits rapid measurements of the concentration of an analyte in a medium to be investigated. By adjusting the flow velocity or the residence time of the transport medium in the analyte feed chamber, the method can be adapted in an advantageously simple way to different analyte concentrations of the medium to be analysed.

If the medium to be analysed does not continuously flow through the analyte feed chamber, but is introduced only at selected times into the analyte feed chamber, it is expedient to add fresh transport medium to the analyte feed chamber only or substantially only when the medium to be analysed is present in the analyte feed chamber.

The analysis apparatus according to the invention includes in further preferred embodiments a plurality of sensors, wherein the sensors may be provided individually or in groups in different sensor chambers. The sensors may all be designed for the same analytes or for different analytes. The apparatus according to the invention accordingly enables a high measurement accuracy to be achieved in a simple way by parallel measurements of analyte concentrations, and in addition enables the concentrations of several analytes to be determined simultaneously. For example, it is thus possible to determine simultaneously the glucose and lactate concentration of a medium to be analysed.

In further preferred embodiments the apparatus according to the invention contains two or more analyte feed chambers, optionally with one or more sensors, in which the analyte feed chambers may be connected in series or possibly, via a further distributor, in parallel. The various analyte feed chambers may in particular contain membranes which permit different analytes from one or various media to be analysed to pass into a transport medium. In this way a particularly good separation of the analytes to be determined can be achieved.

If the analyte feed chambers are arranged in series then, in order to determine an analyte concentration first of all transport medium is passed from the first analyte feed chamber to the sensor and is analysed there. Following this further transport medium is conveyed in the direction of the sensor, until the transport medium from the in each case further analyte feed chamber has arrived in the sensor chamber, where it can be analysed.

When using a plurality of analyte feed chambers connected in parallel first of all an analyte feed chamber is selected, conveniently by means of a distributor, for example a slide valve, from which analyte feed chamber transport medium is to be transferred to the sensor chamber. Transport medium possibly containing analyte is then passed from the analyte feed chamber to the sensor chamber. When using a plurality of analyte feed chambers, in particular connected in parallel, it is also possible to determine an analyte concentration for example at various points in a bioreactor.

An aqueous medium is preferably used as a transport medium. The transport medium is conveniently adapted to the respective analyte(s) and to the respective sensor(s). The transport medium preferably contains a pH buffer. The transport medium preferably also contains (a) a preservative, preferably benzoic acid and/or propionic acid, (b) a surfactant, preferably Triton X and/or Tween 80, and/or (c) an anticoagulant, preferably heparin. The use of a heparin-containing transport medium is in particular preferred for the case where a human or animal body fluid, in particular blood, is to be analysed.

In preferred embodiments of the invention the medium to be analysed is blood. For this purpose an analyte feed chamber in the form of a probe can be introduced into a blood vessel of a patient or an animal to be treated. The analyte feed chamber is connected by a feed line and discharge line to the distributor and to the sensor chamber of an apparatus according to the invention. In this connection the sensor chamber is preferably arranged flush against the analyte feed chamber, in which case it is particularly preferred if the volume of the line, through which the transport medium for the determination of the analyte concentration flows from the analyte feed chamber to the sensor chamber, between the analyte feed chamber and sensor chamber is not more than five times the volume of the analyte feed chamber. In this way a rapid transfer of an analyte-containing, for example glucose-containing, transport medium from the analyte feed chamber to the sensor chamber and a correspondingly rapid measurement can be achieved.

Preferred most of all is an analysis method according to the invention comprising pumping a transport medium by means of a pump in a pumping direction, comprising the following steps:

i) supplying a medium to be analysed to the analyte feed chamber, ii) rinsing a sensor for the substance to be analysed with a transport medium in a first flow direction, wherein the transport medium after the rinsing of the sensor is passed to the analyte feed chamber, iii) charging the transport medium in the analyte feed chamber with an amount of the analyte to be detected, iv) without switching the pumping direction, reversing the flow direction of the transport medium and passing the transport medium, possibly charged with analyte, from the analyte feed chamber to the sensor, v) determining the analyte concentration with the sensor in the sensor chamber, vi) for preparing for a new measurement, rinsing the sensor and preferably also the analyte feed chamber by repeating step ii).

The analysis apparatus according to the invention can in further preferred embodiments be arranged in a bioreactor probe. In this case the analyte feed chamber can be designed for example in the form of a membrane-covered channel, as described in the patent specifications and laid-open specifications mentioned in the introduction. The analyte feed chamber can however also be connected in the form of a shunt or a feed line or discharge line to the bioreactor.

The analyte feed chamber is connected to the sensor chamber via a line for transferring analyte-charged transport medium for determining the analyte concentration, the volume of which is again preferably at most five times the transport medium volume of the analyte feed chamber, in order to allow a rapid transport of the transport medium from the analyte feed chamber to the sensor chamber and therefore a rapid determination of the analyte concentration.

It is furthermore preferred to maintain the analyte feed chamber and/or the sensor chamber at a preselected temperature or in a preselected temperature range by temperature control means.

The invention is described in more detail hereinafter with the aid of the drawings and an example of implementation, without however thereby restricting the scope of protection of the claims, and in which:

FIG. 1A-C is a flow diagram of an analysis apparatus according to the invention;

FIG. 2 is a diagrammatic side view of a combined distributor and a sensor chamber of an apparatus according to the invention;

FIG. 3A-B is a diagrammatic plan view of the distributor and the sensor chamber of FIG. 2;

Figure 1A:
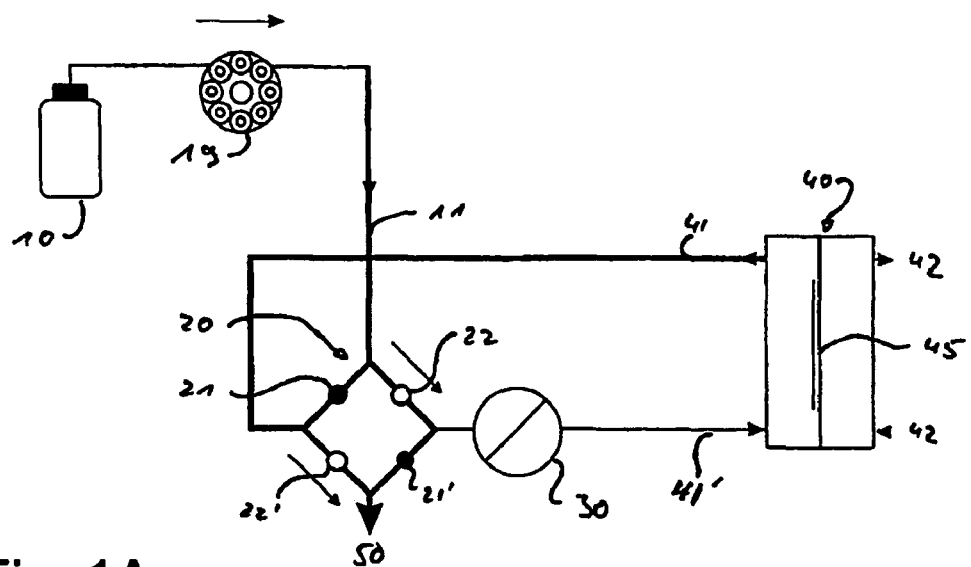

FIG. 1 shows in three partial Figures A to C three operating states of an analysis apparatus according to the invention. The analysis apparatus includes a reservoir 10 for a transport solution. The reservoir 10 is connected via a pump 19, in the illustrated embodiment a peristaltic pump, in the flow connection to a distributor 20. The distributor 20 has an annular channel composed of four segments and including a total of four switching points 21, 21', 22, 22'. The switching points 21, 21', 22, 22' are (not shown here) made in the form of a silicone membrane, which can be pressed in a sealable manner at the respective switching points into the annular channel under the action of compressed air, in order to prevent the transport solution flowing through the respective switching point. At those places at which in each case two of the four segments of the annular channel impact one another, inflow and outflow channels are provided, and more particularly (in the clockwise direction) a feed line 11 from the pump 19, to a sensor chamber 30, to an outlet 50 and to an analyte feed chamber 40. The sensor chamber 30 is connected on the one hand to the distributor 20 and on the other hand, in a flow-type manner, to a feed line 41 of the analyte feed chamber 40, whose discharge line 41' for transport solution is, as mentioned hereinbefore, connected to the distributor 20. The analyte feed chamber 40 includes in addition to the feed and discharge line 41 for transport solution, a feed and discharge line 42 separated therefrom by a membrane 45, for a medium to be analysed. The membrane 45 is able to separate the analyte from the medium to be analysed. In preferred embodiments a membrane 45 is used that retains molecules of size greater than 12000 Da on the side of the medium to be analysed, and simply allows analytes of a size of up to 12000 Da to pass through into the transport medium.

The sensor chamber 30 contains a sensor for detecting the analyte, preferably a biosensor, for example an immobilised glucose oxidase on an amperometric electrode.

To flush the apparatus according to the invention (see FIG. 1A) the switching points 21 and 21' of the distributor 20 are closed by charging with compressed air. Transport medium is conveyed via the pump 19 from the reservoir 10 through the open switching point 22 into the sensor chamber 30, through the analyte feed chamber 40 and from the analyte feed chamber 40 back to the distributor 20. From there transport medium leaves the distributor through the open switching point 22' and reaches the outlet 50, where it is discarded. In this way the sensor chamber 30 and the analyte feed chamber 40 are flushed on the side of the transport medium and the sensor (not shown) of the sensor chamber 30 is freed from analytes possibly contained hitherto in the transport medium. In this way a null calibration of the sensor can be carried out. During the flushing of the sensor chamber 30 and the analyte feed chamber 40, a medium to be investigated can furthermore flow through the analyte feed chamber on the side of the medium to be investigated, though such a throughflow can also be prevented. Since during the flushing no transport medium can reach the sensor chamber 30 from the analyte feed chamber 40, it is therefore not necessary to interrupt the addition of the medium to be analysed.

Figure 1B:
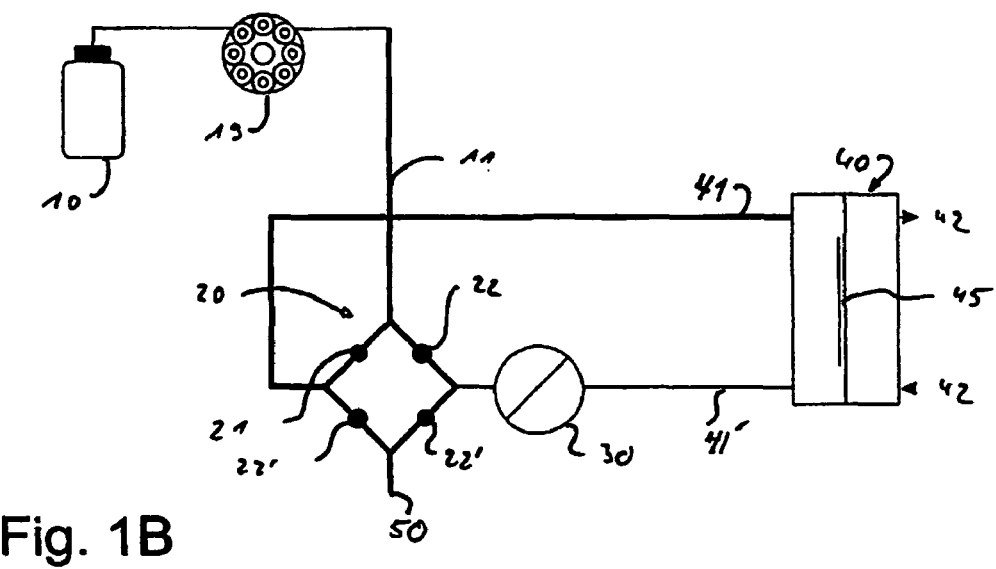

An analyte collection phase of the apparatus according to the invention is shown in FIG. 1B. The pump 19 is switched off so that no transport medium flows through the analyte chamber 40. This analyte feed chamber 40 is now on the side of the medium to be investigated charged with medium to be investigated, for example by the medium to be investigated flowing through the analyte feed chamber 40 on this side. The analyte passes from the medium to be investigated through the membrane of the analyte feed chamber 40 and into the transport medium.

Figure 1C:
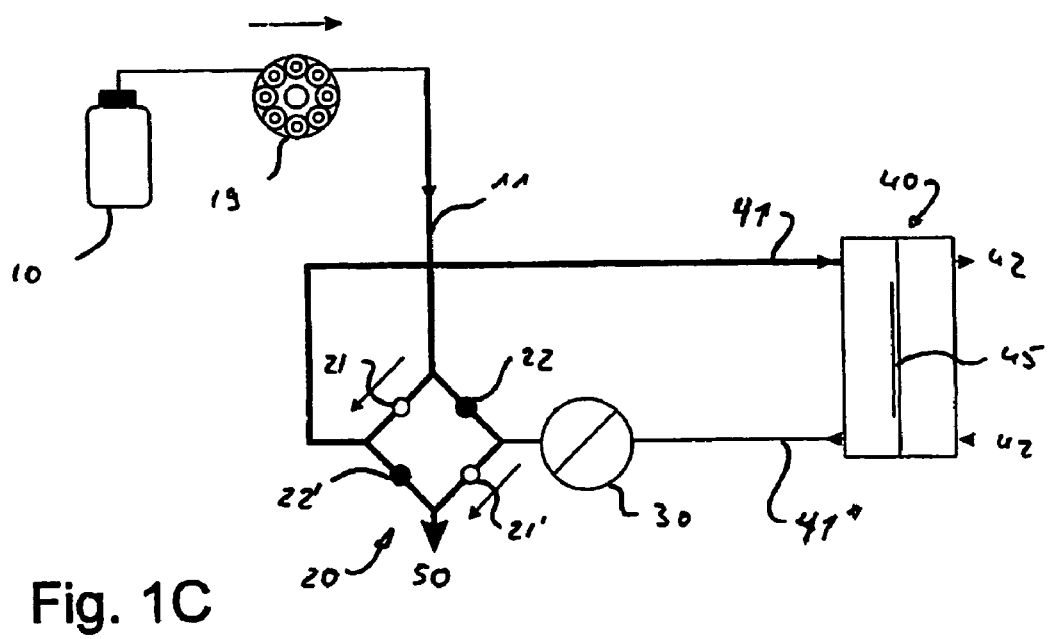

FIG. 1C shows a measurement using an apparatus according to the invention. For this purpose the switching points 21, 21' of the distributor 20 are opened and the switching points 22, 22' of the distributor 20 are closed, preferably as described above by subjecting a silicone membrane to compressed air. The pump 19 pumps transport medium from the reservoir 10 through the feed line 11 into the distributor 20, from where the transport medium flows through the open switching point 21 through the feed line 41 into the analyte feed chamber 40. The analyte-charged transport medium contained in the analyte feed chamber 40 is led from the analyte feed chamber 40 through the line 41' into the sensor chamber 30. The transport medium previously present in the sensor chamber 30 is conveyed from the sensor chamber 30 into the distributor 20 and from there through the open switching point 21' into the outlet 50. The presence of the analyte and preferably its concentration is then measured by the sensor in the sensor chamber 30. The sensor then emits a signal corresponding to the measured parameter, to an output device or processing device (not shown), preferably to a display for displaying the analyte concentration.

When the presence of the analyte or its concentration has been determined by the sensor of the sensor chamber 30, the sensor chamber 30 can be flushed again with transport medium as described hitherto with reference to FIG. 1A. If such a flushing is not desired, further transport medium can in the switching state illustrated in FIG. 1C also be brought via the pump 19 and the distributor 20 through the sample (analyte) feed chamber 40 into the measurement cell 30. In this way a uniform flow of analyte-charged transport medium through the sensor chamber 30 and an ongoing monitoring of the presence and concentration of the analyte are possible. During the whole operation of the apparatus the medium to be investigated remains completely separate from the transport medium, and similarly the transport medium remains separate from the medium to be analysed except for the substances that can pass through the membranes of the analyte feed chamber. The analysis apparatus according to the invention is accordingly particularly suitable for analysing media that have to remain sterile, or from which no other substances apart from the substance to be analysed and smaller substances, should reach the outside.

Figure 2:
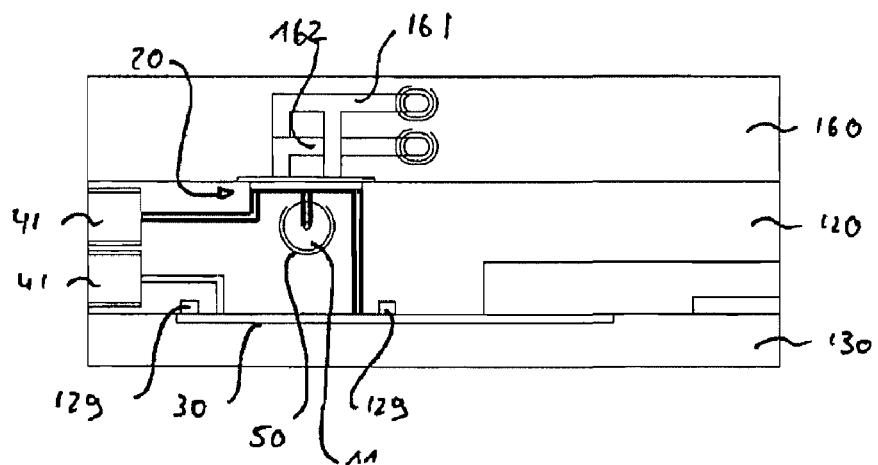
Figure 3A:
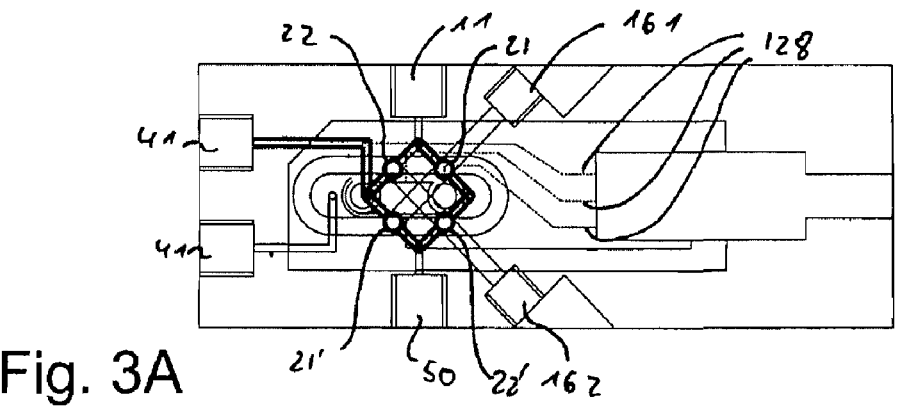
Figure 3B:
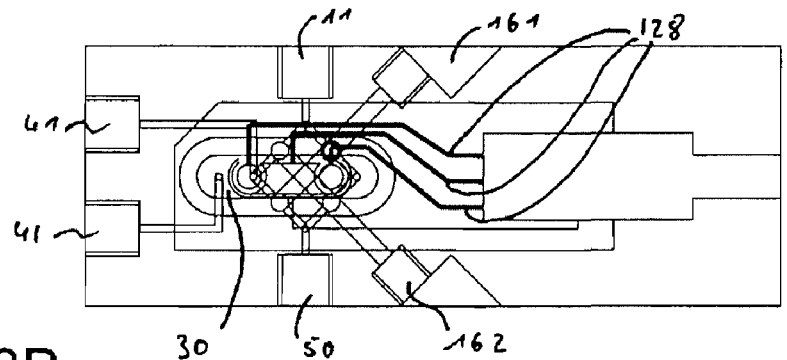

FIG. 2 now shows a diagrammatic side view of a combination of a distributor and a sensor chamber of an apparatus according to the invention, while FIG. 3 shows in two partial FIGS. 3A and 3B a diagrammatic plan view of the structural group shown in FIG. 2. In FIGS. 2 and 3A the distributor 20 with the switching points 21, 21', 22, 22' corresponding to the flow diagram of FIG. 1A is emphasised by thick lines. In FIG. 3B electrical connections to the sensor chamber are emphasised by thick lines. The structural group illustrated in FIGS. 2 and 3 includes no analyte feed chamber 40, but instead connections of the feed and discharge lines 41 for connection to an (external) analyte feed chamber 40. The structural group includes a sensor chamber base body 130. The sensor base body 130 is in liquid-tight contact with a channel base body 120, which contains in particular the channels of the distributor 20 (cf. FIG. 1) and the associated feed lines and discharge lines to the sensor chamber 30 and to the analyte feed chamber 40. The annular channel of the distributor 20 is at the switching points 21, 21', 22, 22' connected in a pressure-tight manner via a membrane to two pressure channels 161, 162 in a switching base body 160.

The channels of the channel base body 120 are effectively connected to corresponding channels and bores of the switching base body 160 and of the sensor chamber base body 130. In the operation of the structural group illustrated in FIGS. 2 and 3 a transport medium is introduced, for example via a pump 19 (shown in FIG. 1), through a feed line 11 into the annular channel of the distributor 20 of the channel base body 120. By charging the pressure channel 161 with compressed air the annular channel is closed in a liquid-tight manner at the switching points 21, 21'. The transport medium then flows through the annular channel of the distributor 20 and a feed line 4 up to an outlet in the direction of the analyte feed chamber 40. Transport medium flowing back from the analyte feed chamber 40 passes through a further channel 41' of the channel base body 120 into the sensor chamber of the sensor chamber base body 130. The sensor chamber of the sensor chamber base body 130 is hermetically connected via a seal 129 to the switching base body 120 so that an outflow of transport medium into a possibly existing gap between the switching base body 120 and the sensor chamber base body 130 is avoided.

A biosensor, for example an amperometric electrode in active conjunction with immobilised glucose oxidase, is arranged in the sensor chamber in order to measure a glucose concentration in the transport medium. The sensor of the sensor chamber 30 generates an electrical signal that is transmitted via electrical connections 128. The electrical connections can be provided in the switching base body and/or in the sensor chamber base body 130. From the sensor chamber 30 the transport medium passes through a channel of the channel base body 120 into the annular channel of the distributor 20, and from there passes through the open switching point 22' and an associated outlet 50 out from the structural group, for example into a waste collecting vessel.

Figure 4:
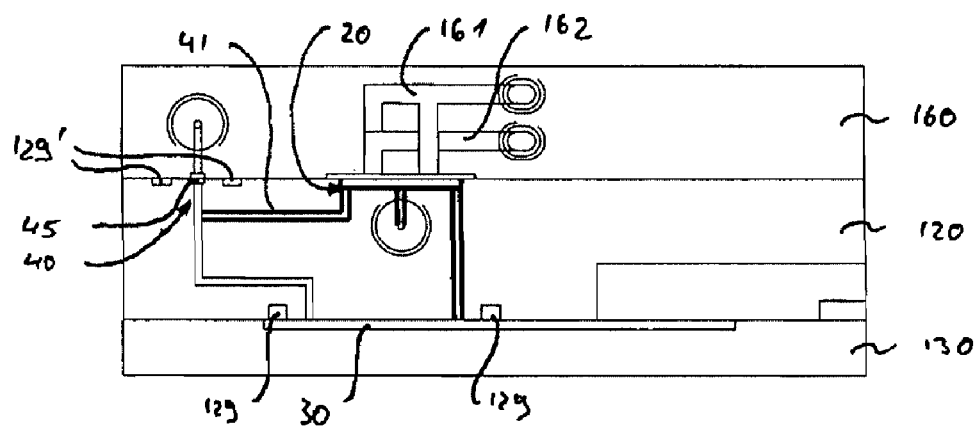
FIG. 4 is a diagrammatic side view of a distributor, a sensor chamber and an analyte feed chamber of an apparatus according to the invention.
Figure 5:
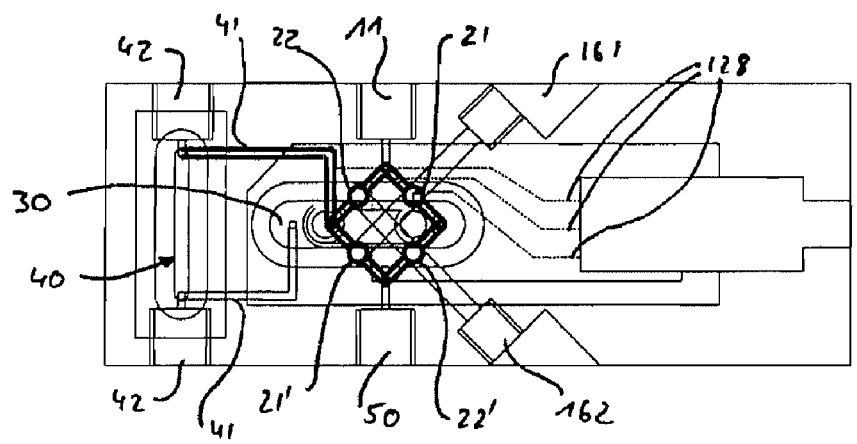
FIG. 5 is a diagrammatic plan view of the distributor, the analyte feed chamber and the sensor chamber of the apparatus shown in FIG. 4.
Figure 6:
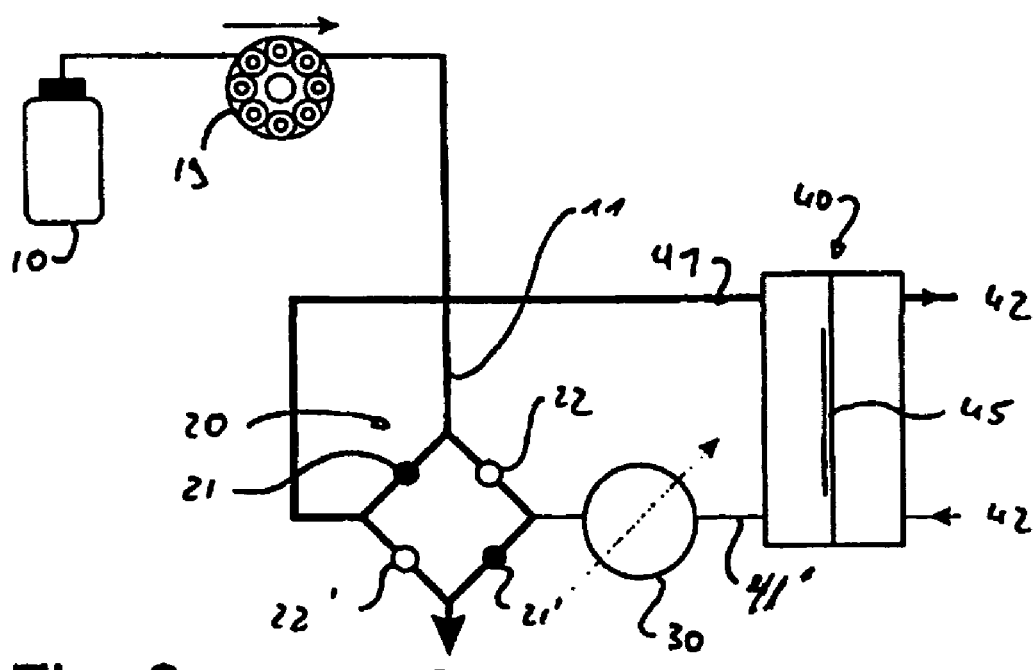
FIG. 6 is a flow diagram of the analysis apparatus according to the invention of FIG. 4.

The structural group according to FIGS. 4 and 5 differs from that of FIGS. 2 and 3 simply in that the analyte feed chamber 40 is part of the structural group. FIG. 6 shows a switching state of the structural group according to FIGS. 4 and 5 corresponding to FIG. 1A, in which again here and in FIGS. 4 and 5 the distributor 20 and the connection of the analyte feed chamber 40 to the distributor 20 are emphasised by thick lines. To form the analyte feed chamber 40 a transport medium channel is provided in the channel base body 120, and on the opposite side a channel for medium to be analysed is provided in the switching base body 160. Both channels are separated from one another by a membrane 45, which allows a substance to be analysed to pass from the medium to be analysed, into the transport medium. Preferably a membrane is used which retains molecules of a size of more than 12000 Da on the side of the medium to be analysed, and simply allows molecules of 12000 Da and less to pass through into the transport medium. The analyte feed chamber 40 is protected by a seal 129' against the leakage of medium to be analysed and transport medium into a possibly existing gap between the switching base body 160 and the channel base body 120. The switching base body contains, unconnected to the pressure channels 161, 162, connections for releasing a medium to be analysed to the analyte feed chamber 40. The structural group of FIGS. 4 and 5 is operated in the corresponding way to the structural group of FIGS. 2 and 3.

Figure 7:
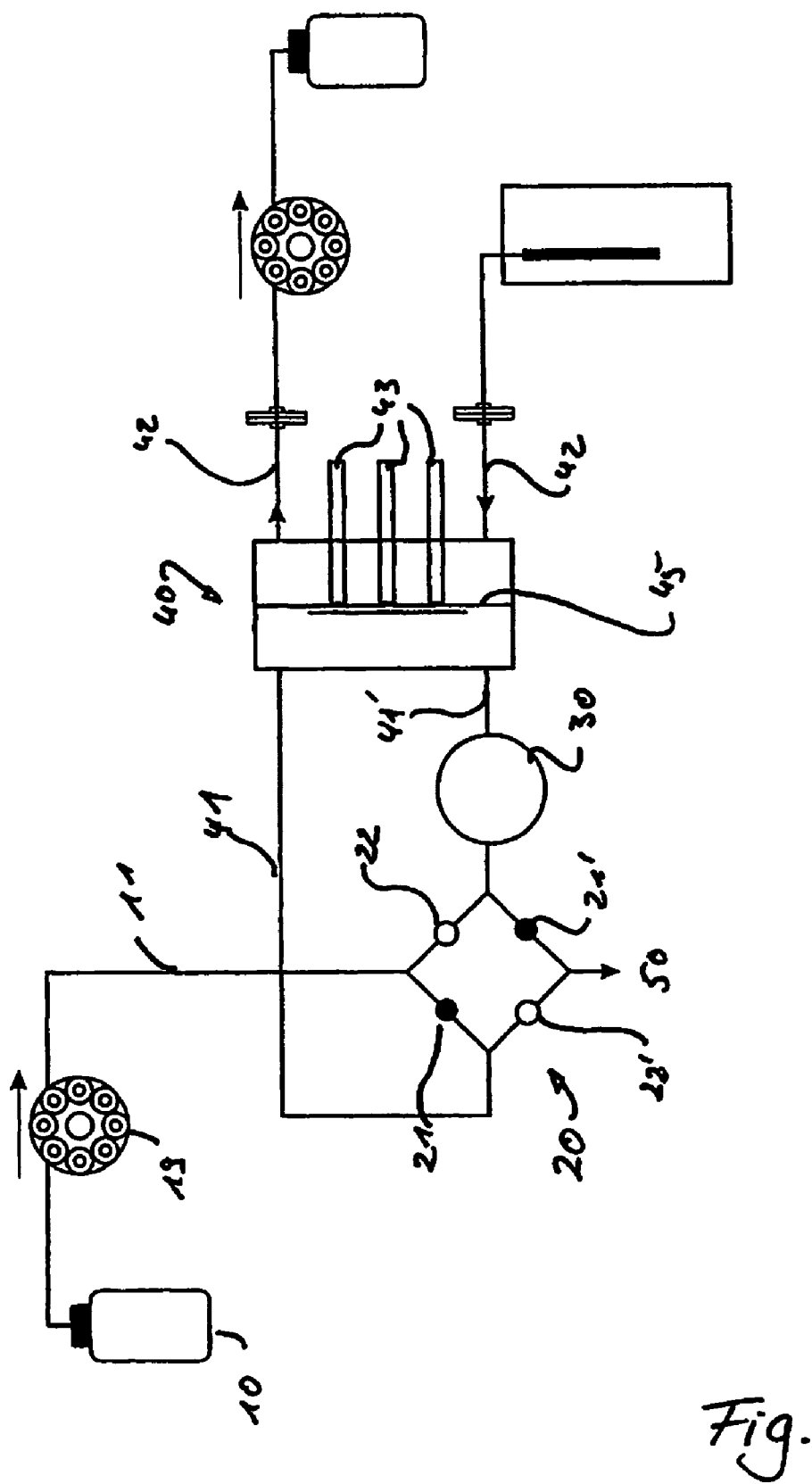
FIG. 7 is a flow diagram of a further analysis apparatus according to the invention.

FIG. 7 shows a further analysis apparatus of the type illustrated in FIG. 1. The analysis apparatus includes in addition three sensors 43. The sensors 43 are arranged in the analyte feed chamber 40, and in the illustrated case on the side of the medium to be analysed. The medium to be analysed is taken from a source, for example a bioreactor or a blood vessel, and is passed through a sterile filter to the analyte feed chamber 40 and to the sensors 43 arranged therein. The medium is pumped continuously or at selected points in time from the analyte feed chamber 40 through a further sterile filter and a pump into a sink, for example a waste collecting vessel. The analysis apparatus is otherwise operated as described above with reference to FIG. 1. In particular the analysis apparatus includes a distributor 20 and a sensor chamber 30, which can be charged with transport medium as described above.

The invention claimed is:

1. Analysis apparatus, comprising
   a) a sensor chamber with a sensor for detecting an analyte in a transport medium,
   b) an analyte feed chamber for receiving the analyte in the transport medium,
   c) a distributor in flow communication with the sensor chamber and the analyte feed chamber, and
   d) a control means for controlling a transport medium flow, wherein the distributor comprises:
   (c1) an annular channel with four connections arranged spaced apart from one another, characterised in that
   (c2) the distributor includes in each case a switchable isolating means between two adjacent connections,
   and the control means is configured to control the distributor in such a way that
      for the flushing, the transport medium is fed from the distributor to the sensor chamber without first passing through the analyte feed chamber, and
      for the measurement, the transport medium is fed from the distributor to the sensor chamber after passing through the analyte feed chamber.

2. Analysis apparatus according to claim 1, wherein each of the switchable isolating means between two adjacent connections is a valve that can be switched by pressure of a control fluid or magnetically.

3. Analysis apparatus according to claim 1, wherein the sensor is selected from the group consisting of an electrochemical or optical sensor.

4. Analysis apparatus according to claim 1, characterised in that the analyte feed chamber is connected to a medium to be analysed via a membrane which permits the passage of the analyte from the medium to be analysed into the transport medium.

5. Analysis apparatus according to claim 1, characterised in that the sensor chamber and the distributor are contained in a unitary structural body.

6. Analysis apparatus according to claim 1, characterised in that the sensor chamber contains two, three or more sensors.

7. Analysis apparatus according to claim 1, characterised in that the analyte feed chamber contains one, two, three or more sensors.

8. Analysis method using the analysis apparatus of claim 1, comprising pumping a transport medium by means of a pump in a pumping direction, comprising the following steps:
   rinsing the sensor for the substance to the analysed with the transport medium in a first flow direction, wherein the transport medium after the rinsing of the sensor is passed to the analyte feed chamber;
   charging the transport medium in the analyte feed chamber with an amount of the analyte to be detected, and
   without switching the pumping direction, reversing the flow direction of the transport medium in order to convey the transport medium, possibly charged with analyte, from the analyte feed chamber to the sensor.

9. A method for determining an analyte concentration in a transport medium, the method comprising passing the transport medium and analyst through the apparatus of claim 1, wherein the analyst is selected from the group consisting of glucose, sucrose, glycerol, methanol, glutamine, glutamate, phosphate, lactate, lactose, ammonium, ethanol, an antibody, pesticide, antibiotic, protein content, fat content, water content, $pO_2$, $pCO_2$ and pH.

10. The method of claim 8, further comprising determining an analyte concentration of glucose, sucrose, glycerol, methanol, glutamine, glutamate, phosphate, lactate, lactose, ammonium, ethanol, an antibody, pesticide, antibiotic, protein content, fat content, water content, $pO_2$, $pCO_2$ and/or pH.

* * * * *